United States Patent [19]

Simbruner

[11] 4,030,492
[45] June 21, 1977

[54] DEVICE FOR SUPPORTING HUMAN BREATHING AND ARTIFICIAL RESPIRATION

[75] Inventor: Georg Simbruner, Vienna, Austria

[73] Assignee: Drägerwerk Aktiengesellschaft, Germany

[22] Filed: Jan. 28, 1976

[21] Appl. No.: 653,148

[30] Foreign Application Priority Data

Feb. 5, 1975 Austria .................... 866/75

[52] U.S. Cl. .................... 128/145.8; 128/351
[51] Int. Cl.² .................... A61M 16/00
[58] Field of Search ........ 128/145.8, 145.7, 145.6, 128/145.5, 188, 194, 147, 186, 351

[56] References Cited

UNITED STATES PATENTS

| | | | |
|---|---|---|---|
| 2,280,050 | 4/1942 | Alexander et al. | 128/145.5 |
| 3,291,122 | 12/1966 | Engstrom et al. | 128/194 |
| 3,504,676 | 4/1970 | Lomholt | 128/351 |
| 3,653,379 | 4/1972 | Glenn | 128/145.6 |
| 3,809,080 | 5/1974 | Deaton | 128/194 |
| 3,881,479 | 5/1975 | Carden | 128/351 |

FOREIGN PATENTS OR APPLICATIONS

| | | | |
|---|---|---|---|
| 2,414,693 | 3/1974 | Germany | 128/145.8 |
| 2,453,490 | 5/1975 | Germany | 128/145.8 |

*Primary Examiner*—Robert W. Michell
*Assistant Examiner*—Henry J. Recla
*Attorney, Agent, or Firm*—McGlew and Tuttle

[57] ABSTRACT

A device for supporting human breathing and artificial respiration particularly for newborn infants by supplying breathing gas to the trachea of the infant comprises a trachea tube which is adapted to be connected into the trachea of the infant and which is connected at its opposite end to a tubular member which defines a pressure chamber therein. The tubular member is opened at its outer end and the pressure inside the tubular member is regulated by directing a jet of breathing gas directly into the pressure chamber within the member in accordance with the pressure condition monitored in the trachea tube. One or more of the gas jets may terminate in the pressure chamber preferably in a direction transverse to the flow passage therethrough from the opening to the trachea tube. The jets may also be used to aspirate moisture into the tube for delivery with the breathing gas to the trachea. The opening of the pressure member may be controlled in accordance with a valve member which may comprise a pivotal disc or an inflatable balloon for example.

10 Claims, 3 Drawing Figures

DEVICE FOR SUPPORTING HUMAN BREATHING AND ARTIFICIAL RESPIRATION

BACKGROUND OF THE INVENTION

1. Field of the Invention

This invention relates in general to devices for facilitating breathing and artificial respiration and in particular to a new and useful device for connection to the trachea of an infant for supporting human breathing or artificial respiration.

2. Description of the Prior Art

In many cases, particularly in diseases of newborn, especially prematurely born, infants, it is necessary to support the breathing or even to have recourse to an artificial respiration. One of the most frequent diseases of newborn infants is the "hyalone-membrane disease" of the lungs where the alveoli collapse because of the high surface tension at a low transpulmonary pressure (i.e. pressure at the respiratory opening minus pleura pressure). This pathophysiological state results in a serious disease aspect and may lead up to a stop of the spontaneous breathing. The therapy in such cases consists in preventing the collapse of the alveoli by an increased transpulmonary pressure. For this purpose, the pressure of the air supplied to the patient is increased to a constant value amounting to between 10 and 150 mm water column, about 50 mm water column on the average, depending on the constitution of the patient. This method is known in the medical practice as the "Continuous Positive Airway Pressure" (CPAP). At a stop of the spontaneous respiration, a mechanical circulation of air is used in which the pressure is periodically varied in accordance with the breathing rhythm. The pressure used in the CPAP is the lower limit of the pressure and during the inspiration period, this pressure is increased to a value necessary for inflating the lungs.

The present invention relates to a device for supporting human breathing and/or artificial respiration, in particular, of prematurely born, newborn and sucking infants, with which the pressure of the breathing gas to be supplied to the lungs can be increased and/or varied in accordance with the respiratory rhythm. The device includes a tracheal tube which is connectable to the trachea and which communicates with a space adapted to be pressurized. The known devices of this kind use a static pressure which is built up in a closed space. This space communicates with the tracheal tube which is inserted into the trachea of the patient and thus connected as tightly as possible therewith. At the application of the CPAP, the necessary constant pressure is maintained in this closed space. This space is connected to the pressure source for the breathing gas which, usually, consists of air enriched with oxygen, and further connected, through a pressure-maintaining valve which, usually, simply comprises a pipe immerged to a corresponding depth below the surface of a water reservoir, to the outer atmosphere. Thus, the breathing gas flows through this space and the expiration gas escapes through the pressure-maintaining valve. Although new, fresh breathing gas is permanently supplied to this space, the dead space is still considerable so that there is a danger, particularly for prematurely born infants, that the patient will inhale stale breathing gas. Known devices of this kind simply comprise a T tube of which one leg is connected to a tracheal tube, the second leg to the supply line for the breathing gas and the third leg to the pressure-maintaining valve. Usually, the perpendicular leg of the T is connected to the tracheal tube and the aligned cross legs are connected to the supply line for the breathing gas and the pressure-maintaining valve, respectively. For purposes of artificial respiration, a valve may be provided which is moved in accordance with the breathing rhythm and establishes the connection, during the inspiration period, between the tracheal tube and the supply line for the breathing gas and, during the expiration period, between the tracheal tube and the pressure-maintaining valve. Aside from the fact that such known devices are complicated and, therefore, expensive, they have the disadvantage that during the use of the device, the tracheal tube is not accessible, since the static pressure must be built up in a closed space. Now, it is necessary to periodically remove mucus by suction and for this purpose, the apparatus must be disconnected and the treatment interrupted which may lead to serious medical complications. Further, the known devices are also susceptible to disturbances. If, for example, the tube leading to the pressure-maintaining valve forms a kink, which may happen time and again, the static pressure in the space continues to linearly increase which may lead to a bursting of the lungs, thus being fatal to the patient. If the supply tube for the breathing gas forms a kink or becomes disconnected, breathing gas is no longer supplied and there is danger of asphyxiation. If, with an artificial respiration, the valve or the valve control fails, then, depending on the position of the valve, in case the tracheal tube remains connected to the pressure-maintaining valve, no fresh breathing gas is supplied to the patient, which may lead to asphyxiation. Also in case the tracheal tube remains connected to the supply line for breathing gas, the pressure in the tracheal tube continues to linearly increase, which may lead to a bursting of the lungs. Consequently, known devices of this kind are disadvantageous and even dangerous.

SUMMARY OF THE INVENTION

In accordance with the invention, at least one gas jet pipe having a permanently open sectional area of flow is connected to a pressurizable space, with the jet directed against the wall of the space, preferably, obliquely against the connection zone between the tracheal tube and this space. At its side opposite to this connection zone of the tracheal tube, the pressurizable space is provided with an opening. Through the gas jet pipe, a dynamic pressure is built up in the pressurizable space. With this space open to the atmosphere, the pressure within the space can never exceed the adjusted dynamic pressure so that a hazard due to a pressure increase is completely eliminated. Since the opening is provided at the side of the pressurizable space remote from the tracheal tube and is permanently open, it is made possible to introduce a probe for removing mucus by suction during operation of the device so that the mucus removal can take place without interrupting the treatment. Both of these advantages are extremely important. Advantageously, in accordance with the invention, the pressurizable space is designed as an integral or separate member with a chamber which is enlarged relative to the tracheal tube. However, this chamber can be of very small size and may, for example, in a device for treating newborn infants, have a diameter of approximately 15 mm and a correspondingly small length in the axial direction of the tracheal tube, the sole purpose of this design being to insure a desired overpressure under the effect of the inflowing breathing gas. With this provision, the dead space is relatively small so that the patient is repeatedly supplied with fresh breathing gas.

For a treatment in accordance with the CPAP method, such a design is satisfactory. If, however, an artificial respiration is to be provided, the pressure must be periodically increased, in synchronism with the breathing rhythm, from the CPAP level up to a value necessary for the inflation of the lungs. For this purpose, in accordance with the invention, the opening which is provided at the side of the pressurizable space opposite to the tracheal tube and which, advantageously, is formed by a tubular socket, may be made closable, in accordance with the breathing rhythm, by means of a shut-off member. As long as the shut-off member is in opening position, only the dynamic pressure takes effect in the pressurizable chamber. This corresponds to the pressure level necessary for the CPAP. If, however, the shut-off member is in closing position and the breathing gas is supplied through the jet pipe into the pressurizable chamber which is closed, the pressure increases to a level which is sufficient to inflate the lungs and, thus, to effect the artificial inspiration. The shut-off member is controlled so as to prevent exceeding of the necessary pressure. With the shut-off member open, a probe for mucus removal by suction can be introduced and during the period of this removal, at least the CPAP treatment may be continued. In such cases, however, there is still a theoretical possibility of a failure of the control of the shut-off member and of a necessity of interrupting the artificial respiration during the suction period, with the treatment limited to the CPAP.

Therefore, in accordance with a preferred embodiment of the invention, a jet pipe conveying a breathing gas is provided projecting into the tracheal tube or into a tubular extension thereof, with the jet directed approximately parallel to the axis of the tracheal tube, and the gas supply through this jet pipe is made controllable in accordance with the breathing rhythm. In this case, no shut-off member is provided for the pressurizable space in the opening connecting the space to the atmosphere and this opening remains permanently open. Consequently, with the opening permanently open, there is no need for interrupting the artificial respiration during the introduction of a probe for removing mucus by suction. The overpressure necessary for the artificial respiration during the inspiration period is again produced dynamically, by means of the jet pipe having its jet directed approximately in the axial direction of the tracheal tube, wherefore, in this case again, since the system is open, the admissible inflating pressure cannot be exceeded and the patient cannot be endangered. Now, the possibility of a failure of the control of the breathing-gas supply to the jet pipe located in the tracheal tube or the tubular extension thereof is still to be taken into account. In such a case, with the inventive device, a remedial measure is still possible. That is, the physician himself can control the breathing rhythm manually by closing the opening connecting to the atmosphere periodically with his finger in accordance with the breathing rhythm, with the result that during the closing period, the static pressure in the pressurizable space increases to the value necessary for inflating the lungs. At the same time, the jet pipe having its axis approximately parallel to that of the tracheal tube may be connected to another available pressure source so that the supply pressure of the breathing gas may be increased as desired. In consequence, the inventive device offers the greatest possible security in operation. In order to facilitate the introduction into the tracheal tube of the probe for removing the mucus by suction without interrupting the treatment, the jet pipe having its axis parallel to that of the tracheal tube is positioned close to the inside surface of the tracheal tube or the tubular extension thereof, so that the inside cross-sectional area of the tracheal tube is left largely clear.

In accordance with the invention, the opening provided at the side of the pressurizable space remote from the tracheal tube is approximately coaxial of the tracheal tube and, preferably, formed by a tubular socket. The alignment with the tracheal tube has the advantage that the probe for the mucus removal can be easily introduced and the design in the form of a tubular socket facilitates, in case of need, the closure of this opening with a finger.

Advantageously, the gas jet pipe connected to the pressurizable space is located so as to project into the chamber and the orifice of a tube for supplying moisture is located in the zone of the orifice of the gas jet pipe. Water may be supplied in atomized form or in the form of vapor or humid air, the supplied moisture being taken in by the injector effect of the gas jet pipe. It is also possible, however, to provide a supply of moisture to the tracheal tube or the tubular extension thereof, through a tube provided in the zone of the orifice of the jet pipe having its jet directed in the axial direction of the tracheal tube. In this case again, the moisture is taken in due to the injector effect of the jet pipe.

According to a development of the invention, at a location downstream of and spaced from the orifice of the jet pipe having its jet directed parallel to the axis of the tracheal tube, a sensor line may be connected for sensing the pressure in the tracheal tube. This sensor line may lead to a control device which is usual in known apparatus for the supporting of breathing or for artificial respiration and which, ordinarily, is built up of so-called fluidic elements. Through this control device, the supply of breathing gas to the jet pipe provided in the tracheal tube or the tubular extension thereof is controlled in accordance with the breathing rhythm and as a function of the pressure within the tracheal tube. The purpose of locating the connection of the sensor line to the tracheal tube at a distance downstream of the orifice of the jet pipe is to pick up the actual pressure in the tracheal tube without distortion through the dynamic pressure or the injector effect of the jet.

In all embodiments, the gas jet pipe projecting into the pressurizable space may be provided with an obliquely cut orifice and mounted for rotation. Due to the orifice formed by an end obliquely cut off, the jet discharged from the pipe becomes unsymmetrical so that, in this way, the direction of the jet and thereby, its dynamic effect, can be varied while the orifice remains at the same location, independently of the angular position.

Accordingly, it is an object of the invention to provide an improved device for supporting human breathing and artificial respiration particularly for newborn infants by supplying breathing gas to the trachea of the infant, comprising a tracheal tube having an end communicating with the trachea and an opposite open end and with a pressure chamber defined within the tube which communicates with the trachea and the open end and with at least one breathing gas jet conduit terminating in a jet discharge into the pressure chamber for regulating the breathing gas pressure therein.

A further object of the invention is to provide a device for supporting human breathing and artificial respiration which is simple in design, rugged in construction and economical to manufacture.

For an understanding of the principles of the invention, reference is made to the following description of typical embodiments thereof as illustrated in the accompanying drawings.

DESCRIPTION OF THE PREFERRED EMBODIMENTS

Figure 1:
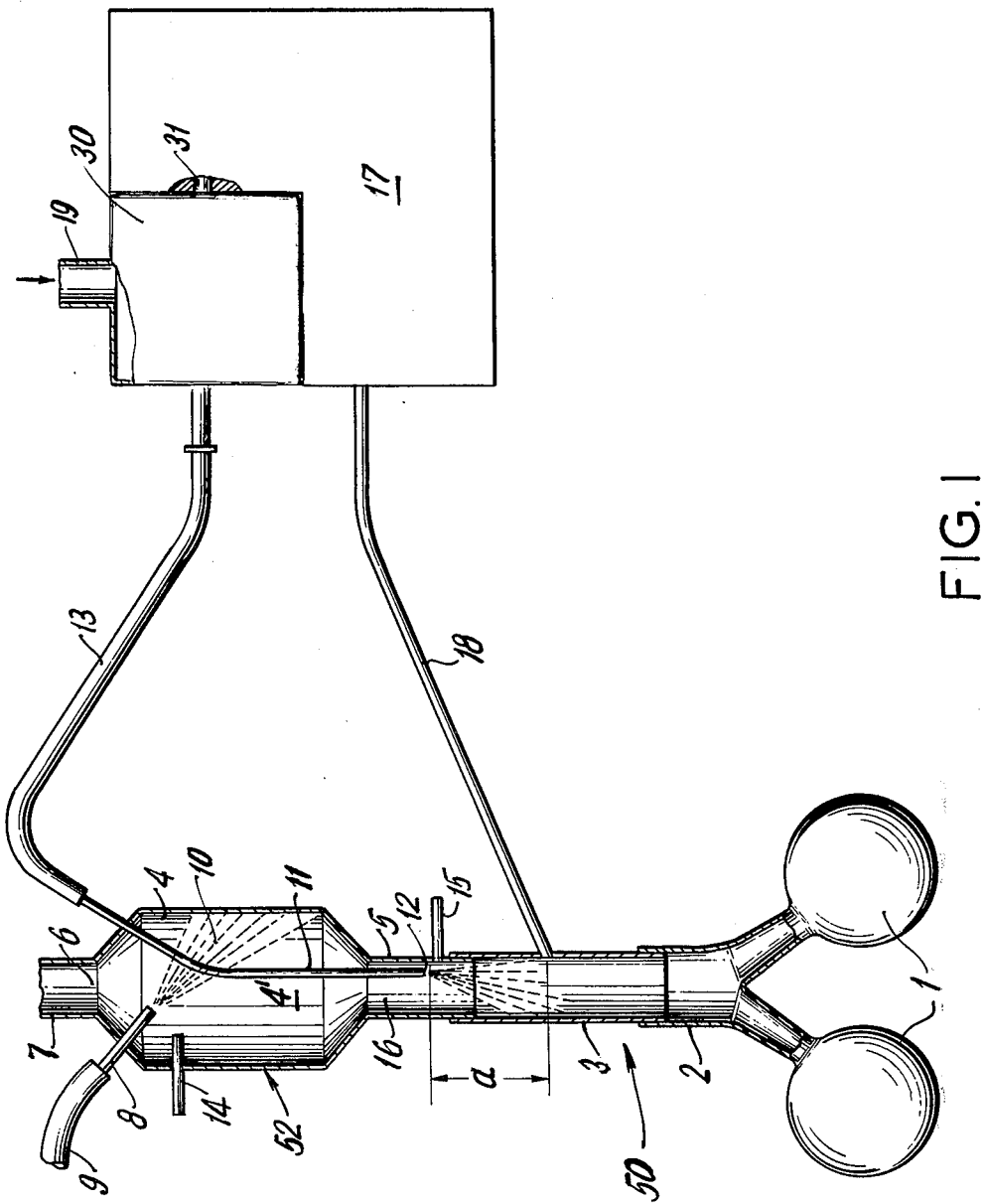
FIG. 1 is a diagrammatical representation of a device for supporting human breathing and artificial respiration constructed in accordance with the invention.

Referring to the drawings in particular the invention embodied therein in FIG. 1 comprises a device for supporting human breathing and artificial respiration generally designated 50 which includes tracheal tube means generally designated 52 having a tracheal tube portion 3 having one end connected into a trachea 2 which is connected to the lungs 1 of the person whose breathing must be supported or who must be respirated. The trachea tube means in the embodiments shown includes a separate member 4 forming an enlarged pressure chamber 4' which is connected to the opposite end of the trachea tube portion 3 through a tubular extension 5 therebetween. The opposite end is provided with an opening 6 which is limited by a tubular socket 7 and through which the chamber 4' continuously communicates with the atmosphere. The cross-sectional area of the opening 6 is equal to or larger than the cross-sectional area of flow of the tubular extension 5.

In accordance with the invention a breathing gas line 9 is provided with an end having a jet pipe 8 which discharges into the chamber 4' so that a breathing gas jet 10 is directed against a wall of the pressure chamber 4'. A second breathing gas line 13 is provided with a jet pipe 11 which has a discharge orifice 12 located in the tubular extension 5 directly alongside a moisture supply hose 15 so that the jet created thereby produces an induced flow through the moisture supply line 15. The jet pipes 8 and 11 are designed as thin, hollow needles and have diameters of for example from 0.9 to 1.2 mm.

The jet 10 is advantageously made to impinge on the walls of the pressure chamber 4' and it produces an overpressure in the chamber 4' which is maintained in spite of the permanently opened opening 6 and it may correspond to a water column pressure of 10 to 150 mm. Thereby the pressure necessary for a CPAP treatment is produced in the chamber 4'. For a CPAP treatment this is sufficient since no artificial respiration is required.

The jet pipe 11 is supplied with breathing gas through the line 13 under a pressure of approximately 0.25 to 2.5 atmospheres in excess. By the jet discharged from the jet pipe 11 through the orifice 12 the pressure in the tracheal tube portion 3 is increased to a value sufficient to inflate the lungs 1 and thus to compensate for the inspiration.

A moisute supply line 14 is also located in the orifice zone of the jet pipe 8 so that moisture will be taken in by the injector effect of the jet 10 similar to the action of the jet discharged from the orifice 12 in respect to the supply line 15. The jet pipe 11 is positioned close to the wall of the tubular extension 5 so that at 16 a free passage cross-sectional area remains for the introduction of a probe having to remove mucus by suction. Tubular socket 7 is coaxial to the tracheal tube portion 3 and this facilitates the introduction of such a probe for the removal of mucus. Since the opening 6 in the embodiment of FIG. 1 is opened permanently the probe can be introduced without interrupting the treatment.

The apparatus shown in FIG. 1 also advantageously includes a control 17 provided with so-called fluidic elements and which is used in the known respirators in clinics. A sensor line 18 communicating with the control device 17 is connected to tracheal tube 3 at a location spaced by a distance $a$ from the orifice 12 of the jet pipe 11 downstream thereof. The distance $a$ is approximately from 20 to 40 mm and the arrangement makes it possible to pick up the static pressure at this location of the tracheal tube 3. The pressure variations which are picked up control the supply of breathing gas to the jet pipe 11 through the connecting tube 13. Breathing gas supply line 19 is connected to a valve 30 which is controlled through a connection 31 by the control device 17. In the embodiment shown the valve 30 may be easily disconnected from the control device so that it can be replaced and sterilized at any time.

In the known apparatus it is necessary to preheat the breathing air. In the inventive device since the jet pipes 8 and 11 have a very small diameter and the air is blown in at very high speed, the air passing through the pipes 8 and 11 is heated up to a degree sufficient for preheating purposes. Jet pipe 8 opens into the chamber 4' near the opening 6 so that the injector effect of the discharge jet 10 includes to a certain extent also the zone of the opening 6 so that a higher overpressure can be obtained in the chamber 4'.

Figure 2:
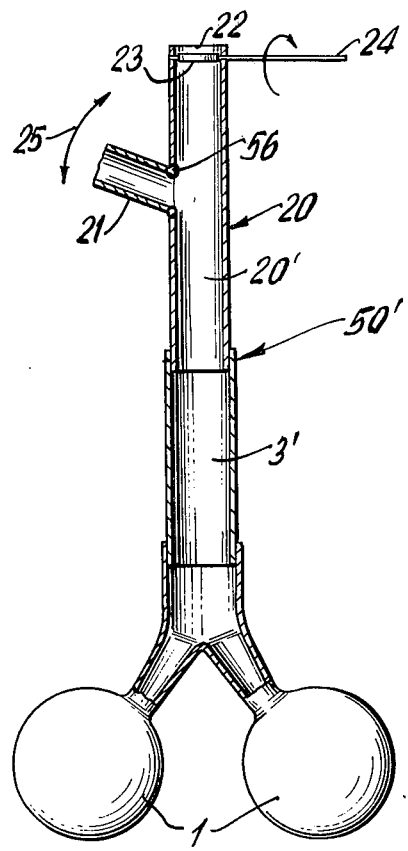
FIGS. 2 and 3 are are views similar to FIG. 1 showing other embodiments of the invention.

In the embodiment shown in FIG. 2 a device for supporting human breathing and artificial respiration generally designated 50' includes a tracheal tube portion 3' and a tubular member 20 forming an interior pressure chamber portion 20' which communicates with the tracheal tube 3' and also with an opening 22 at the opposite side of the tubular member 20. Pressurized breathing gas is supplied through a tube 21 which is pivotally connected at 56 to the tubular member 20 so that it may be adjusted in position in the direction of the arrow 25 for varying the pressure in the chamber 20'. The angle may be set so as to produce a dynamic pressure corresponding to the CPAP pressure in the chamber 20'. In such a case the opening 22 is closed by a shut-off member which comprises a rotatable disc 23 which is driven through a flexible shaft 24. The size of the disc 23 may be such that it does not completely close the opening 22. The disc during its rotation closes and opens the opening two times during each revolution and thus half the revolution corresponds to one period of the breathing rhythm and this breathing rhythm is controlled by a control device (not shown) which is similar to the control device shown in FIG. 1. By making the disc 23 smaller than the size of the outlet 23 it can be assured that even in the closing position the opening 22 will not be completely closed. The tube 21 may be shifted during operation so as to vary the dynamic pressure produced in the chamber 20'.

Figure 3:
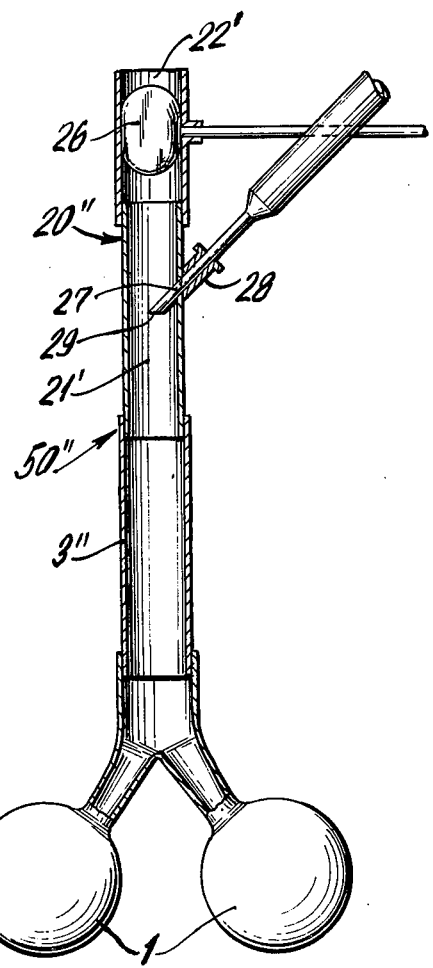

In the embodiment shown in FIG. 3 a device for supporting human breathing artificial respiration generally designated 50" includes the tracheal tube portion 3" which is connected to the lungs 1 of the user and also to a tubular member 20" which defines an interior pressure chamber 21'. In this embodiment the opening 22" is closable by an inflatable member or balloon 26 which may be inflated and deflated in accordance with the breathing rhythm. In this embodiment a jet pipe 27 is mounted to extend through a guide 28 so as to be rotatable therein about an axis which is at an angle to the axis of the tracheal tube portion 3". The orifice 29 of the jet pipe 27 is obliquely cut so that the discharge jet is unsymmetrical. By turning the jet pipe 27 the direction of the jet and thereby the value of the dynamic pressure can be adjusted independently of the total respiration volume to be administered.

While specific embodiments of the invention have been shown and described in detail to illustrate the application of the principles of the invention, it will be understood that the invention may be embodied otherwise without departing from such principles.

What is claimed is:

1. A device for supplying human breathing and artificial respiration, comprising a tracheal tube having one first tubular end connectible to the person's trachea, an opposite second tubular end connectible to atmosphere and an intermediate tubular portion connected between said one tubular end and said opposite tubular end and defining an interior pressure chamber therein, said one tubular end, said pressure chamber and said opposite tubular end defining a continually opened flow passage therethrough, at least one first breathing gas conduit connected into said pressure chamber and discharging breathing gas across said flow passage to provide a constant pressure in said tracheal tube, and at least one second breathing gas conduit connected into said pressure chamber and having a discharge extending substantially axially toward said first tubular end with respect to said flow passage, and control means connected to said second breathing gas conduit for controlling the gas supply thereto in accordance with the respiration rhythm.

2. A device for supplying human breathing and artificial respiration to a person's trachea, comprising a tracheal tube having one first tubular end connectible to the person's trachea, an opposite second tubular end connectible to atmosphere and an intermediate tubular portion connected between said one tubular end and said opposite tubular end and being of a wider diameter than said tubular portions at each end and defining an interior pressure chamber therein, said one tubular end, said pressure chamber, and said opposite tubular end defining a continuous opened flow passage therethrough, at least one breathing gas conduit connected into said pressure chamber and discharging breathing gas across its flow passage to provide a constant pressure in said tracheal tube, and at least one second breathing gas line connected into said second tubular end having a discharge extending substantially axially toward said first tubular end thereby discharging breathing gas into said flow passage.

3. A device according to claim 2, wherein said tracheal tube is of a diameter sufficient to permit a clear passage therethrough and past said breathing gas conduit and said second breathing gas conduit.

4. A device according to claim 2, including a moisture supply line connected into said trachea tube in the vicinity of said second breathing gas conduit discharge so as to introduce moisture into the trachea tube means by the action of the discharge of the breathing gas.

5. A device according to claim 2, wherein aid least one second breathing gas conduit extending parallel to said trachea tube, and at least one moisture supply connected into said trachea tube in the vicinity of said second breathing gas conduit so as to produce the induced inflow of moisture thereto.

6. A device according to claim 2, wherein said at least one breathing gas conduit is oriented to discharge in a direction substantially parallel to the axis of said tracheal tube means, and a sensor line for sensing the pressure within said tracheal tube means connected to said tracheal tube means downstream of said discharge.

7. A device according to claim 2, including means for closing said opening and for opening said opening in accordance with the breathing rhythm.

8. A device for supplying human breathing and artificial respiration to a person's trachea, comprising a tracheal tube having one first tubular end connectible to the person's trachea, an opposite second tubular end terminating in an opening connectible to atmosphere and an intermediate tubular portion connected between said one tubular end and said opposite tubular end and defining an interior pressure chamber therein, said one tubular end, said pressure chamber and said opposite tubular end defining a flow passage therethrough, at least one first breathing gas conduit connected into said pressure chamber and discharging breathing gas across said flow passage to provide a constant pressure in said tracheal tube, means for closing and opening said opening in said second tubular end in accordance with the respiration rhythm including a rotatable disc, means for rotating said disc at a time corresponding to the respiration rhythm so that, as the disc moves through one half a revolution between a completely closed position and a completely open position.

9. A device according to claim 8, wherein said at least one breathing gas conduit terminates in a jet discharge which extends obliquely in respect to the axis of said conduit, said conduit being rotatable to vary the orientation of the discharge exit in said pressure chamber.

10. A device for supplying human breathing and artificial respiration to a person's tracheal, comprising a tracheal tube having one first tubular end connectible to the person's tracheal, an opposite second tubular end terminating in an opening connectible to atmosphere and an intermediate tubular portion connected between said one tubular end and said opposite tubular end and defining an interior pressure chamber therein, said one tubular end, said pressure chamber and said opposite tubular end defining a flow passage therethrough, at least one first breathing gas conduit connected into said pressure chamber and discharging breathing gas across said flow passage to provide a constant pressure in said tracheal tube, means for closing and opening said opening in said second tubular end in accordance with the respiration rythm including an inflatable and deflatable valve member located in said second tubular end of said tracheal tube.

* * * * *